United States Patent [19]

Kwiatek et al.

[11] Patent Number: 5,503,844
[45] Date of Patent: Apr. 2, 1996

[54] FOAM LAMINATE TRANSDERMAL PATCH

[75] Inventors: Alfred Kwiatek, Bal Harbour, Fla.;
Ludwig J. Weimann, Burlington, Vt.;
Wayne C. Pollock, Riverton, N.J.;
Sharad K. Govil, Essex, Vt.

[73] Assignee: MLI Acquisition Corp. II, Morgantown, W. Va.

[21] Appl. No.: 63,515

[22] Filed: May 18, 1993

[51] Int. Cl.⁶ .................... A61F 13/00; A61F 13/02
[52] U.S. Cl. .................... 424/449; 424/434; 424/447; 424/448; 521/159; 521/172; 521/174
[58] Field of Search .................... 424/434, 447, 424/448, 449; 604/304, 307; 602/56, 58; 521/62

[56] References Cited

U.S. PATENT DOCUMENTS

| | | | |
|---|---|---|---|
| 4,573,996 | 3/1986 | Kwiatek et al. | 604/897 |
| 4,597,961 | 7/1986 | Etscorn | 424/28 |
| 4,710,191 | 12/1987 | Kwiatek et al. | 604/897 |
| 4,820,525 | 4/1989 | Leonard et al. | 424/486 |
| 4,839,174 | 6/1989 | Baker et al. | 424/447 |
| 4,911,916 | 3/1990 | Cleary | 424/449 |
| 5,016,652 | 5/1991 | Rose et al. | 131/270 |

*Primary Examiner*—Jyothsna Venkat
*Attorney, Agent, or Firm*—Lerner, David, Littenberg, Krumholz & Mentlik

[57] ABSTRACT

Devices for the controlled release of an active agent to the skin or mucosa of a host are disclosed, which devices are laminates of a cellular foam layer having a first surface and a second surface, which foam layer has an active agent incorporated therein; a backing layer having an inner surface and an outer surface, wherein the inner surface is affixed to the second surface of the foam layer so that the active agent cannot permeate from the second surface of the foam layer through the outer surface of the backing layer; and means for affixing the laminate to the skin or mucosa of the host so that the active agent is capable of being continuously released from the first surface of the foam layer thereto. Methods for assembling the laminate devices are also disclosed, as are methods in which the foam layer is formed from a prepolymer solution on the backing layer. Methods are also disclosed for the polymerization of cellular urethane foams having active agents uniformly dispersed therethrough.

43 Claims, 5 Drawing Sheets

FOAM LAMINATE TRANSDERMAL PATCH

BACKGROUND OF THE INVENTION

The present invention relates to a device for the controlled release of an active agent to a host. In particular, the present invention relates to transdermal delivery patches that are laminates having a cellular foam layer containing an active agent. More particularly, the present invention relates to transdermal devices for the topical application of active agents such as nicotine.

Transdermal administration systems are well-known in the art. Occlusive transdermal patches for the administration of an active agent to the skin or mucosa are described in U.S. Pat. Nos. 4,573,996, 4,597,961 and 4,839,174.

One type of transdermal patch for the administration of an active agent is disclosed in U.S. Pat. No. 5,016,652. In this case, an absorbant pad is covered on its upper surface by an occlusive layer, with the lower surface coated with an adhesive to affix the pad to the skin. The pad is disclosed as being a somewhat absorbant material capable of functioning as a reservoir, and is formed of a cotton, non-woven or similar cloth-like material capable of retaining, but yet dispensing, a liquid carrier. The pad may also be formed of a silicone polymer matrix of a cross-linked silicon rubber and having micro-sealed compartments which are effectively formed by the in situ cross-linking of the silicon rubber. The efficient production of patches having uniform transdermal release rates and other desirable properties is problematic with patches of this type, particularly when the pad is formed of cotton, non-woven or a cloth-like material.

Another type of transdermal patch for the administration of an active agent is disclosed in U.S. Pat. No. 4,597,961. In this case, a patch is disclosed in which an occlusive backing is formed having a cavity, located within which is a suitable absorbant material, such as a sponge, non-woven or cotton. The occlusive layer extends peripherally beyond the cavity and the peripheral area is coated with an adhesive for affixing the patch to the skin. Cotton and sponge reservoirs are undesirable because they possess non-uniform rate of release. Again, the efficient production of patches of this type having a uniform and consistent release rate is problematic.

There remains a need for improved transdermal patches having absorbant layers that function as carriers for active agents. A transdermal patch having this structure that can be produced efficiently with little variation in release rate and other transdermal properties from patch to patch would be highly desirable.

SUMMARY OF THE INVENTION

This need is met by the present invention. It has now been discovered that cellular foams are particularly suitable for use as carrier layers for active agents in transdermal patches. Cellular foams can be laminated to occlusive backings to produce transdermal patches having a high degree of patch-to-patch uniformity and consistency for critical transdermal properties such as release rate.

Therefore, according to one embodiment of the present invention, a device is provided for the controlled release of an active agent to the skin or mucosa of a host, which device is a laminate of:

(a) a cellular foam layer having a first surface and a second surface, said foam layer comprising an active agent incorporated therein;

(b) a backing layer having an inner surface and an outer surface, the inner surface of which is affixed to the second surface of the foam layer so that the active agent cannot permeate from the second surface of the foam layer to the outer surface of the backing layer; and (c) means for affixing the laminate to the skin or mucosa of the host so that the active agent is continuously released from the first surface of the foam layer thereto.

In one aspect of this embodiment, a rate-controlling means is laminated to the first surface of the foam layer to control the rate at which the active agent is released to the skin or mucosa of the host. A preferred means for accomplishing this is provided by a rate-controlling polymer layer laminated to the first surface of the foam layer, which rate-controlling polymer layer is capable of controlling the rate at which the active agent is released from the first surface of the foam layer to the host's skin or mucosa.

The laminated patch may be attached to the skin or mucosa of the host by an active agent permeable adhesive layer adapted to adhere the laminate to the skin or mucosa of the host, affixed to the rate-controlling polymer layer on the surface opposite the foam layer. This adhesive layer may or may not control the rate at which the active agent is released from the first surface of the foam layer to the host's skin or mucosa.

Preferably, the laminate of this invention will also include a transporting agent or flux enhancer to promote the penetration of the active agent through the skin. Active agent flux enhancers suitable for use in transdermal delivery patches are well-known, and are described, for example, in U.S. Pat. No. 4,573,996, the disclosure of which is hereby incorporated herein by reference thereto.

According to another aspect of this embodiment of the invention, the above-described backing layer extends peripherally beyond the foam layer about the entire periphery thereof so as to create an extended peripheral area of the backing layer, the inner surface of which extended peripheral area of the backing layer is laminated with an adhesive layer to adhere the laminate to the skin or mucosa of the host.

As with the other aspects of this embodiment discussed above, the laminate can also include a rate-controlling polymer layer affixed to the first surface of the foam layer. The laminate may or may not be attached to the host on the outer surface of the rate-controlling polymer layer by an active agent permeable adhesive layer that may or may not control the rate at which the active agent is released from the first surface of the foam layer to the host's skin or mucosa.

In another embodiment of the present invention, a method is provided for assembling a device for the controlled release of an active agent to the skin or mucosa of a host, which method includes the steps of:

(a) incorporating an active agent into a cellular foam layer having a first surface and a second surface;

(b) providing a backing layer having an inner surface and an outer surface and laminating the second surface of the foam layer to the inner surface of the backing layer so that a laminate of the foam layer and the backing layer is formed wherein the active agent cannot permeate from the second surface of the foam layer to the outer surface of the backing layer; and (c) providing the laminate with means for securing the laminate to the skin or mucosa of the host so that the active agent is controllably released from the first surface of the foam layer thereto.

According to one aspect of this embodiment of the invention, the step of laminating the second surface of the foam layer to the inner surface of the backing layer includes the step of laminating the second surface of the foam layer to the inner surface of a backing layer having a greater surface area than the foam layer so that the greater surface area of the backing area extends peripherally beyond the foam layer about the entire periphery thereof so as to create an extended peripheral area of the backing layer. The step of providing the laminate with means for securing the foam layer to the skin or mucosa of the host then includes the step of laminating the extended peripheral area of the inner surface of the backing layer with an adhesive layer to adhere the laminate thereto.

In accordance with one aspect of this embodiment of the present invention, the inner surface of the backing layer is a material capable of adhering to urethane foam formed thereon and the laminating step includes the steps of:

(a) providing a prepolymer solution of a polyisocyanate;

(b) contacting the polyisocyanate solution with an effective quantity of an aqueous solution comprising a urethane catalyst; and (c) coating the solution mixture between the inner surface of the backing layer and a retaining layer so that the solution mixture forms a microcellular urethane foam layer affixed to the inner surface of the backing layer without an adhesive.

In the above-discussed aspect of this embodiment of the present invention, the step of incorporating the active agent preferably includes the step of adding the active agent to either the prepolymer solution or the aqueous solution before the step of adding the urethane catalyst, depending upon the solubility of the active agent, so that the active agent is incorporated into the foam layer as it is formed on the inner surface of the backing layer.

In accordance with one aspect of either of the two above-described methods of the invention, rate-controlling means can be provided by laminating to the first surface of the foam layer, a rate-controlling polymer layer capable of controlling the rate at which the active agent is released from the first surface of the foam layer to the host's skin or mucosa. Either method may further include the step of applying to the rate-controlling polymer layer on the surface opposite the foam layer an active agent permeable adhesive layer adapted to adhere the laminate to the skin or mucosa of the host. The active agent permeable adhesive may or may not control the rate at which the active agent is released from the first surface of the foam layer to the host.

In still yet another embodiment of the present invention, a method is provided for forming a cellular urethane foam having an active agent uniformly dispersed therethrough, which method includes the steps of:

(a) providing a solution comprising a polyisocyanate; and (b) contacting said polyisocyanate solution with an effective quantity of an aqueous solution comprising an active agent and a urethane catalyst, so that the solution mixture forms a cellular urethane foam having the active agent uniformly dispersed therein.

One aspect of this embodiment of the invention coats the prepolymer solution between a first layer and a retaining layer so that the prepolymer solution forms a cellular urethane foam of uniform thickness. Preferably, the surface of the first layer is a backing layer capable of adhering to the urethane foam formed thereon, so that the foam is laminated to the surface of the backing layer without an adhesive.

The present invention includes the discovery that absorbant cellular foams are suitable for use as liquid active agent carriers in transdermal delivery patches. The patches are formed by laminating the foam to an occlusive backing layer. With the present invention, it is possible to manufacture transdermal delivery patches having an absorbant foam layer for active ingredients with improved uniformity from patch to patch in delivery rates and other transdermal properties compared to the transdermal patches of the prior art incorporating absorbant layers of sponge, non-woven, cellulosic materials, cotton or other cloth-like materials. Transdermal delivery patches of the present invention incorporating absorbant cellular foam layers can also be prepared more economically, not only because of the high degree of patch-to-patch uniformity and reduced production of "reject" patches, but also because the cellular foams, unlike the sponge, non-woven, cotton, cellulosic and other cloth-like materials of the prior art, can be laminated on high speed laminating equipment, or cast directly on the laminate, with or without incorporation of the active ingredients.

BRIEF DESCRIPTION OF THE DRAWINGS

A more complete appreciation of the invention and many other intended advantages can be readily obtained by reference to the following detailed description when considered in connection with the following drawings, wherein.

It should be noted that the drawings are not necessarily to scale, but that certain elements have been expanded to show more clearly the various aspects of the present invention and their advantages.

DETAILED DESCRIPTION OF THE PREFERRED EMBODIMENTS

The devices in accordance with the present invention provide for the controlled release of an active agent to the skin or mucosa of a host. The devices are laminates containing a cellular foam layer as the carrier for the active agent.

The active agent may be incorporated into the cellular foam carrier layer by one of two very different types of techniques. By one technique the foam is first formed before receiving the active agent by sheet casting or by being peeled from bun stock. Pre-peeled roll stock is also commercially available.

Regardless of how the foam carrier layer is formed, this technique requires the active agent to be incorporated into the foam in a liquid vehicle, together with any flux enhancers or other modifiers. Adhesive lamination of foam layers containing active agents in liquid vehicles to backing layers of other films is difficult to perform in a manner that will prevent attack by the liquid vehicle on the adhesive layer. Pre-formed foams are therefore preferably laminated by flame-bonding of the foam layer to the adjacent layers prior to incorporation of the active agent.

One way to accomplish adhesive lamination of flame-bonded foams by this technique, however, is to first flame bond the foam to a film layer. The film layer is then adhesive laminated to an adjacent layer. Film layer materials are chosen to prevent migration of the liquid vehicle to the adhesive.

The second technique polymerizes the foam directly on an adjacent layer or between adjacent layers, eliminating the need for adhesive lamination. In addition, the active agent may be added to the pre-foam solution prior to formation of the foam layer, so that a liquid vehicle for the active agent is not needed and adhesive lamination may be readily employed. Thus, the foam layer may be formed by polymerization of a solution containing the active agent against one or two release liners and adhesive laminated to one or two adjacent layers. An adhesive layer may also be applied to a foam layer thus formed to provide a means for affixing the laminate to the skin or mucosa of a host. The availability of adhesive lamination for this technique is important when flame bonding is not possible because of potential pyrolysis of the active agent.

Figure 1:
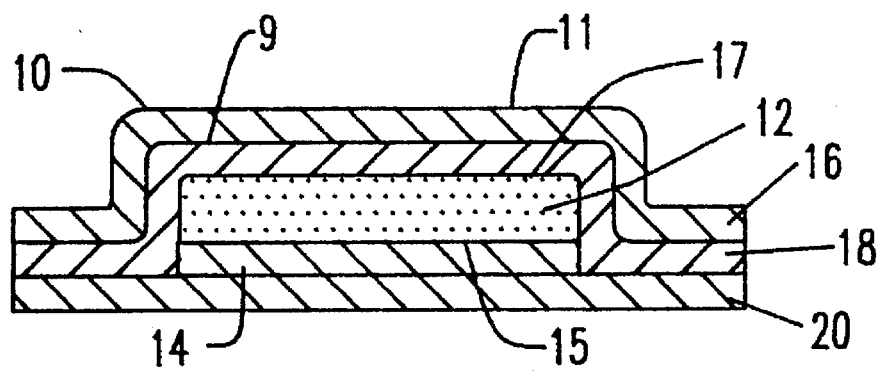
FIGS. 1–1a show side, cross-sectional views of a device according to the present invention.

Referring to the figures, in which like numerals refer to like portions thereof, FIG. 1 shows a device according to the present invention. FIG. 1 shows a cross section of the entire transdermal delivery patch device 10 of the present invention in its sealed configuration. The active agent is contained in an absorbant cellular foam layer 12, which was polymerized with the active agent in the prepolymer solution. The active agent may be combined with an active agent flux enhancer, which functions to promote the penetration of the active agent through the skin.

An active agent permeable skin contact adhesive layer 14 is applied to surface 15 of the foam layer 12, providing a means for affixing the device to the skin or mucosa of the host. The inner surface 9 of backing layer 16 is affixed by adhesive layer 18 to the surface 17 of the foam layer 12. Either the backing layer 16, or the adhesive layer 18, or both, should be occlusive, that is, impermeable to the active agent so that the active agent does not permeate outwardly through the outer surface 11 of the backing layer.

Protective liner 20 covers adhesive layers 14 and 18 prior to use to prevent the release of active agent and to protect the adhesive layers, which are pressure-sensitive adhesives, from inactivation by ambient dust or other contaminants.

The backing layer 16 and the adhesive layer 18 have a sufficient surface area and are of a shape so that, when they are attached to the foam layer 12, they overlap the foam layer 12 completely. Thus, the adhesive surface adheres to the foam layer 12 so that the adhesive layer 18 surrounds the perimeter of the foam layer 12 and the active agent permeable skin contact adhesive layer applied to surface 15 thereof.

The active agent permeable adhesive layer 14 and the adhesive layer 18 are positioned so that when the protective liner 20 is removed, the two adhesive layers can be applied to the skin or mucosa and thus function as a means for affixing the device to the host. The active agent is thus released from surface 15 of foam layer 12 through the active agent permeable skin contact adhesive layer 14 to provide a continuous dose of the active agent therethrough, but cannot permeate through the backing layer 16, or when the adhesive layer 18 is active agent impermeable, radically outwardly therethrough.

Figure 1A:
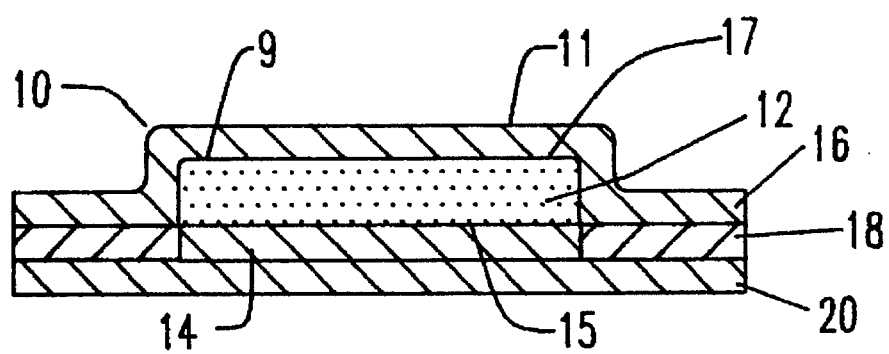

The embodiment shown in FIG. 1a differs from that in FIG. 1 only in that backing layer 16 is affixed to surface 17 of foam layer 12 by formation of foam layer 12 on the inner surface 9 of backing layer 16. Therefore, backing layer 16 is occlusive, that is, impermeable to the active agent so that the active agent does not permeate outwardly through the outer surface 11 of occlusive backing layer 16.

Figure 2:
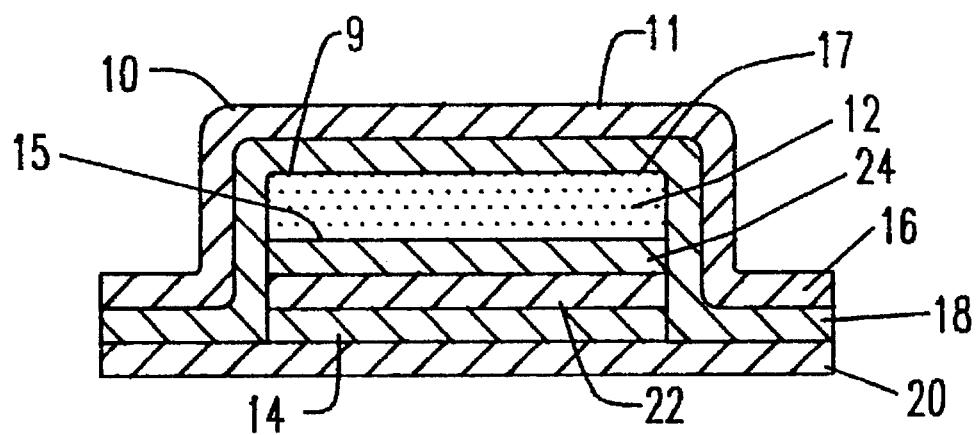
FIG. 2 shows a side, cross-sectional view of a related embodiment of the present invention.

The embodiment shown in FIG. 2 differs from that in FIG. 1 only in that a rate-controlling polymer layer 22 is affixed to surface 15 of foam layer 12 by active agent permeable adhesive layer 24 to provide a means for controlling the rate at which the active agent is released from the surface 15 of foam layer 12 to the skin or mucosa of the host. In FIGS. 1, 1a and 2, any or all of the adhesive layers 14 or 24, or the rate-controlling polymer layer 22 may optionally include an active agent flux enhancer to promote the penetration of the active agent through the skin.

With respect to FIG. 2, active agent permeable skin contact adhesive layer 14 is applied to the surface of the rate-controlling polymer layer 22 opposite the foam layer 12 to provide additional means for affixing the device to the skin or mucosa of the host. Means for controlling the rate at which the active agent is released from the surface 15 of the foam layer 12 to the skin can also be provided to the embodiment of FIG. 1 by utilizing an adhesive capable of controlling the rate at which the active agent is released from the surface 15 of the foam layer 12 to the host's skin or mucosa as the active agent permeable skin contact adhesive layer 14.

Figure 3:
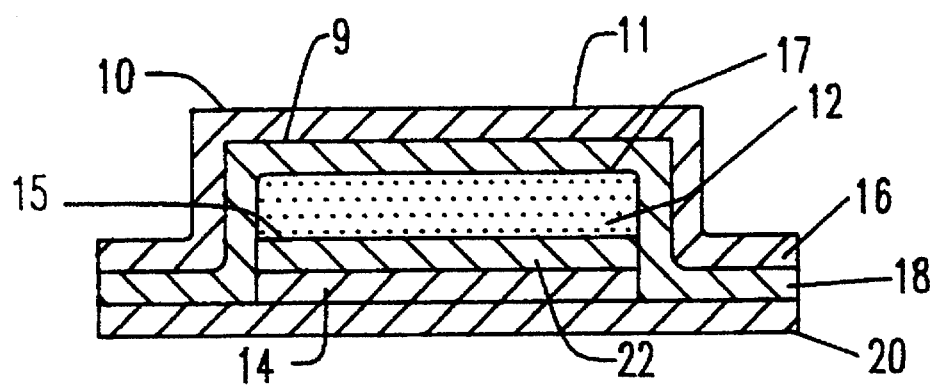
FIG. 3 shows a side, cross-sectional view of a related embodiment of the present invention.

The embodiment shown in FIG. 3 differs from that in FIG. 2 in that rate-controlling foam layer 12 has been polymerized on surface 5 of polymer layer 22. Additional means for affixing the device to the skin or mucosa of the host is provided by active agent permeable skin contact adhesive layer 14 applied to the surface of the rate-controlling polymer layer 22 opposite the foam layer 12.

Figure 4:
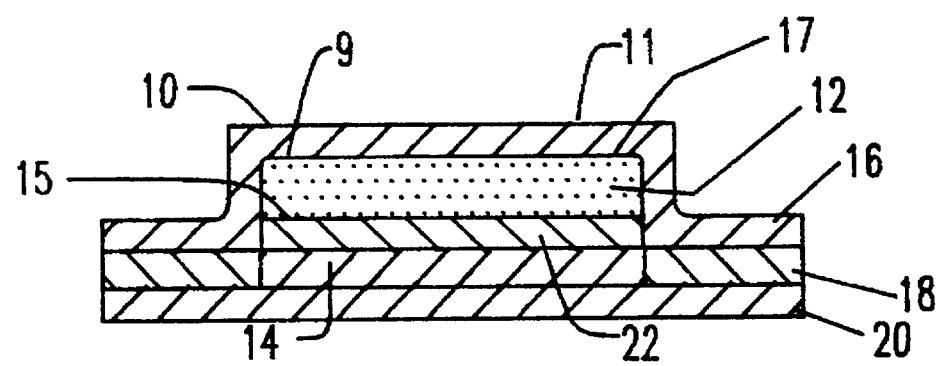
FIG. 4 shows a side, cross-sectional view of a related embodiment of the present invention.
Figure 5:
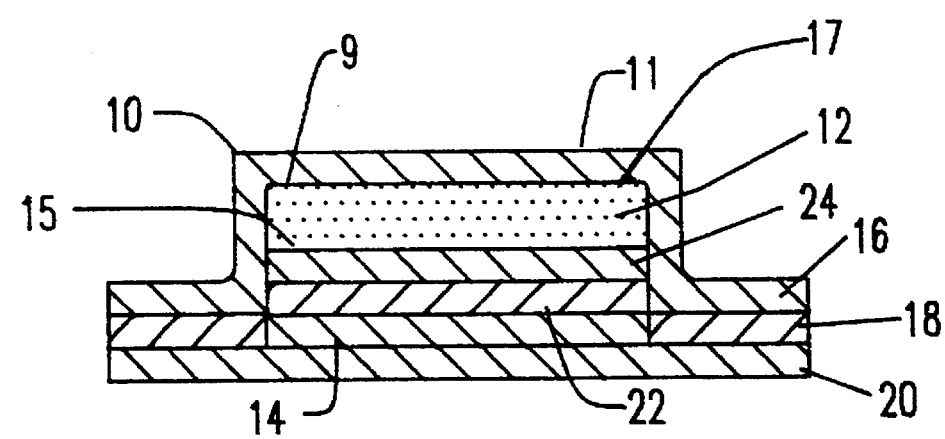
FIG. 5 shows a side, cross-sectional view of a related embodiment of the present invention.

The embodiment shown in FIGS. 4 and 5 differs from that in FIGS. 3 and 2, respectively, only in that backing layer 16 is affixed to surface 17 of foam layer 12 by formation of foam layer 12 on inner surface 9 of backing layer 16. In either embodiment, the backing layer 16 is occlusive, that is, impermeable to the active agent so that the active agent does not permeate outwardly through the outer surface 11 of occlusive backing layer 16.

The adhesive layer 18 is applied to surface 9 of backing layer 16 so as to surround the perimeters of the foam layer 12, the rate-controlling polymer layer 22 and the adhesive layer 14. Adhesive layers 14 and 18 are positioned so that when the protective liner 20 is removed, the two adhesive layers can be applied to the skin or mucosa and thus function as a means for affixing the device to the host. The active agent is thus released from surface 15 of foam layer 12 through the active agent permeable skin contact adhesive layer 14 to provide a continuous dose of the active agent therethrough, but cannot permeate through the backing layer 16 or adhesive layer 18, which is an active agent impermeable adhesive.

The devices shown in FIGS. 3–5 may optionally include a flux enhancer to promote the penetration of the active agent through the skin. The flux enhancer may be included with any or all of the foam layer 12, the rate-controlling polymer layer 22 or the adhesive layers 14 or 24, whichever are present. The foam layer 12 may also require that a binder be used in combination with the active agent in order that the active agent be adequately retained within the layer.

Figure 6:
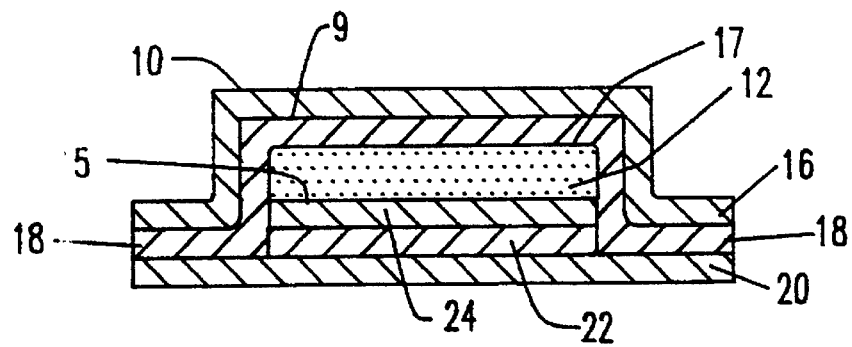
FIGS. 6–6a show side, cross-sectional views of two other related embodiments of the present invention.
Figure 6A:
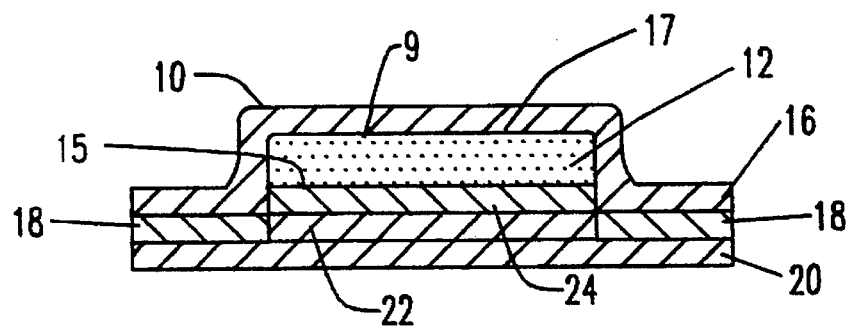

The embodiment shown in FIG. 6 differs from that in FIG. 2 in that rate-controlling polymer layer 22 is directly applied to the host's skin or mucosa. Adhesive layer 18 in this embodiment is the sole means for affixing the laminate to the host. The embodiment shown in FIG. 6a differs from that in FIG. 6 only in that an occlusive backing layer 16 is affixed to surface 17 of foam layer 12 by formation of foam layer 12 on the inner surface 9 of occlusive backing layer 16. Adhesive layer 18 in this embodiment is limited to the extended peripheral area of backing layer 16 surrounding the perimeter of foam layer 12 and rate-controlling polymer layer 22.

Figure 7:
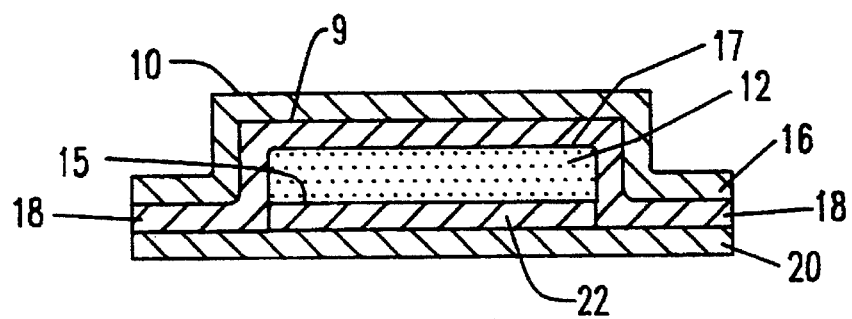
FIGS. 7–7a show side, cross-sectional views of two other related embodiments of the present invention.
Figure 7A:
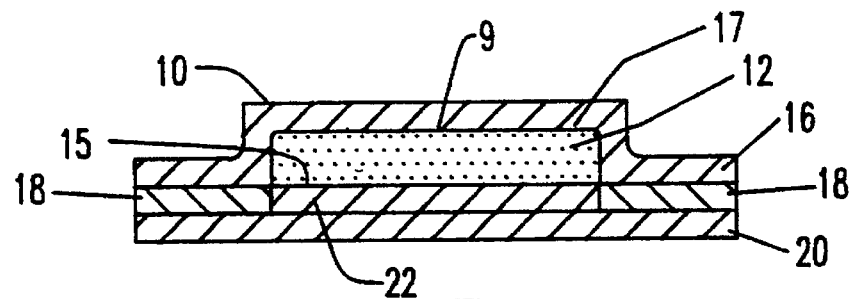

The embodiment shown in FIG. 7 likewise differs from that in FIG. 3. Rate-controlling polymer layer 22 is directly applied to the host's skin or mucosa. Adhesive layer 18 is the sole means for affixing the laminate to the host. The embodiment shown in FIG. 7a differs from that in FIG. 7 in that an occlusive backing layer 16 is affixed to surface 17 of foam layer 12 by formation of foam layer 12 between surface 15 of rate-controlling polymer layer 22 and surface 9 of occlusive backing layer 16. Again, in this embodiment, adhesive layer 18 is limited to the extended peripheral area of backing layer 16, surrounding the perimeter of foam layer 12 and rate-controlling polymer layer 22.

Figure 8:
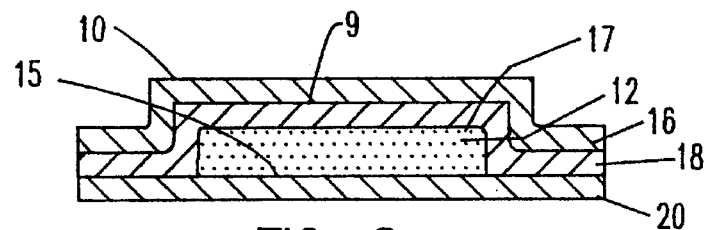
FIGS. 8–8a show side, cross-sectional views of two other related embodiments of the present invention.
Figure 8A:
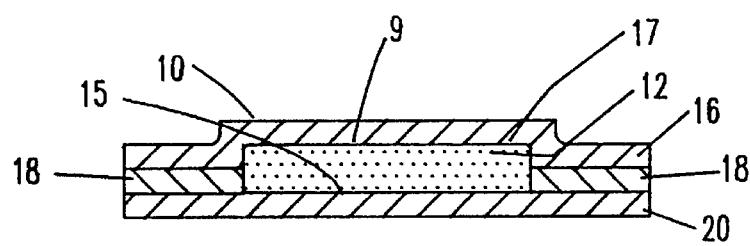

The embodiment shown in FIG. 8 differs from that in FIG. 2 in that foam layer 12 is directly applied to the host's skin or mucosa, with adhesive layer 18 the sole means for affixing the laminate to the host. The embodiment shown in FIG. 8a differs from that in FIG. 8 only in that occlusive backing layer 16 is affixed to surface 17 of foam layer 12 by formation of foam layer 12 on the inner surface 9 of occlusive backing layer 16. Once again, adhesive layer 18 is limited to the extended peripheral area of backing layer 16, surrounding the perimeter of foam layer 12.

Figure 9:
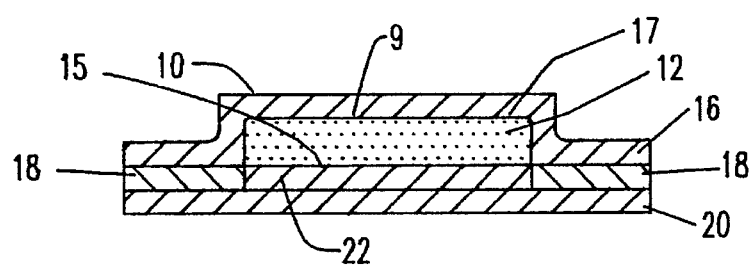
FIGS. 9–9b show side, cross-sectional views of three other related embodiments of the present invention.

The device 10 shown in FIG. 9 is somewhat similar to that shown in FIG. 4. Absorbant cellular foam layer 12 containing the active agent has an occlusive backing layer 16 affixed thereto at surface 17. Occlusive backing layer 16 is affixed to surface 17 by formation of foam layer 12 on inner surface 9.

Figure 9A:
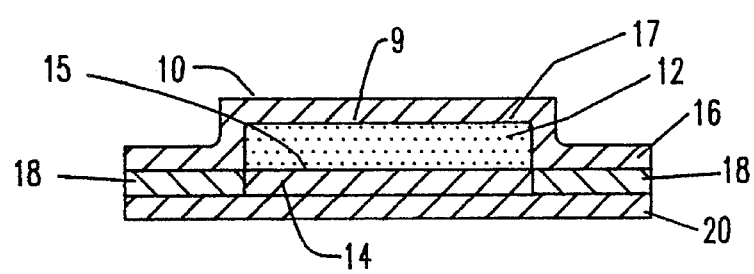
Figure 9B:
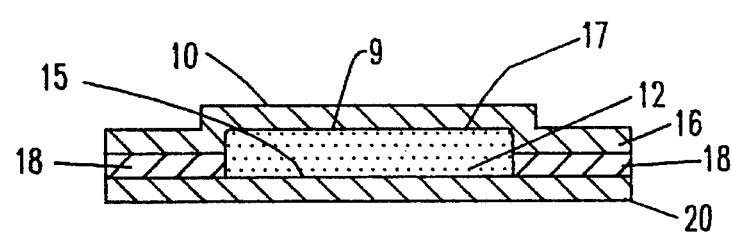

The embodiment shown in FIG. 9 differs from that in FIG. 4 in that the rate-controlling polymer layer 22 is directly applied to the host's skin or mucosa. Adhesive layer 18 is thus the sole means for affixing the laminate to the host. The embodiment shown in FIG. 9a differs from that in FIG. 9 in that adhesive layer 14 directly adheres foam layer 12 to the host's skin or mucosa. The embodiment shown in FIG. 9b differs from that in FIG. 9a in that foam layer 12 is in direct contact with the host's skin or mucosa. Adhesive layer 18 is again the sole means for affixing the laminate to the host.

Figure 10:
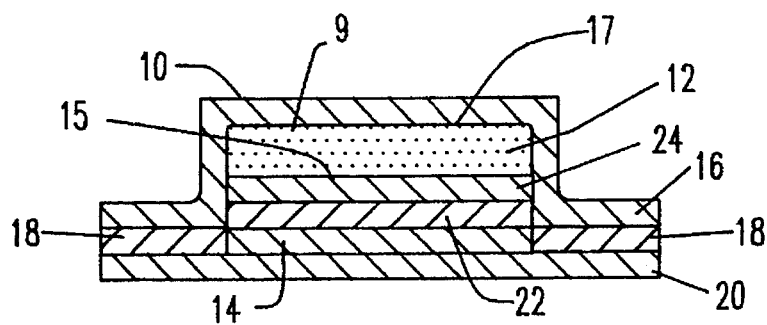
FIGS. 10–10a show side, cross-sectional views of two other related embodiments of the present invention.
Figure 10A:
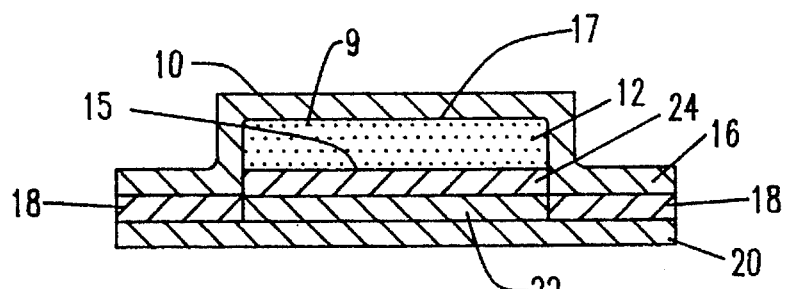

The embodiment shown in FIG. 10 differs from that in FIG. 9 in that adhesive layer 24 affixes rate-controlling polymer layer 22 to surface 15 of foam layer 12. Adhesive layer 14 is applied to the surface of the rate-controlling polymer layer 22 opposite the foam layer 12. The embodiment shown in FIG. 10a differs from that in FIG. 10 only in that rate-controlling polymer layer 22 is directly applied to the host's skin or mucosa. Adhesive layer 18 is again the sole means for affixing the laminate to the host.

Figure 11:
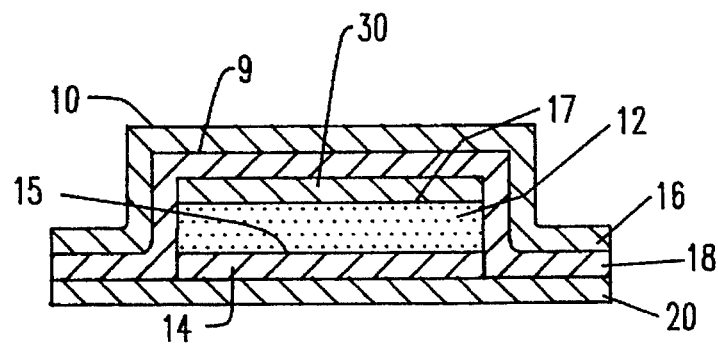
FIGS. 11–11a show side, cross-sectional views of two other related embodiments of the present invention.
Figure 11A:
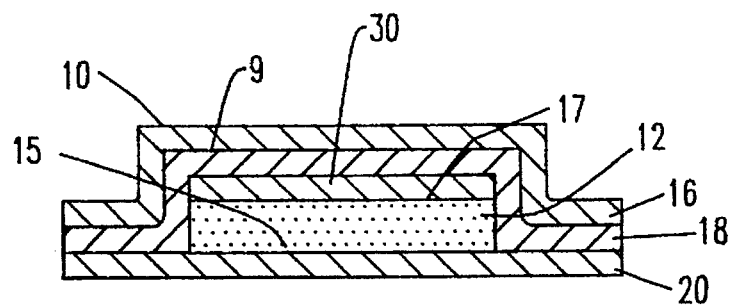

The embodiment shown in FIG. 11 differs from that in FIG. 1 in that foam layer 12 has been flame-bonded to film layer 30. Film layer 30 is affixed to the inner surface 9 of backing layer 16 by adhesive layer 18. Any or all of the backing layer 16, the adhesive layer 18 or the film layer 30 should be occlusive, that is, impermeable to the active agent so that the active agent does not permeate outwardly through the outer surface 11 of the backing layer. The embodiment shown in FIG. 11a differs from that in FIG. 11 in that foam layer 12 is in direct contact with the host's skin or mucosa, similar to the embodiment of FIG. 7. The embodiments of FIGS. 2, 3, 6 and 8 may be similarly varied by the inclusion of the same film layer between the foam layer 12 and adhesive layer 18.

The devices shown in FIGS. 6–11a may likewise optionally include a flux enhancer to promote the penetration of the active agent through the skin. The flux enhancer may be included with any or all of the foam layer 12, the rate-controlling polymer layer 22 or the adhesive layers 14 or 24, whichever are present. The foam layer 12 may also require that a binder be used in combination with the active agent in order that the active agent be adequately retained within the layer.

The backing layer is preferably a thin film or sheet. In many instances, because of the area of skin to which the device is to be attached, the device, and therefore the backing layer, is flesh-colored for cosmetic reasons. Preferably, it is a clear polyester layer, which is occlusive with respect to the active agent, but it can be dyed various colors, or include printed matter thereon. The backing layer normally provides support and a protective covering for the device.

The backing layer is preferably made of a material or combination of materials that is substantially impermeable to the layer or layers with which it can be in contact, i.e., to the foam layer and the active agents contained therein, the adhesives, etc. However, a primary objective is to prevent seepage of the active agent through the backing layer of the device so, if the backing layer is coated on the surface in contact with the remainder of the device with an adhesive layer that is active agent impermeable, this impermeable adhesive layer will perform this purpose even if the backing layer is not totally impermeable to the active agent. Thus, it is not necessary in all instances that the backing layer be impermeable to the active agent, although in most instances it normally is, and when it is not a layer providing this barrier function, such as an active ingredient impermeable adhesive layer, will be situated between the backing layer and the foam layer. By substantially impermeable, it is meant that the other components in contact with the backing layer or component under consideration will not appreciably permeate through such layer or component for the normal period of use and storage of the device.

The actual material used for the outer surface layer, i.e., referring to FIG. 1, for example, the backing layer 16, would depend on the properties of the materials in contact therewith. Some suitable materials include, for example, cellophane, cellulose acetate, ethyl cellulose, plasticized vinyl acetate-vinyl chloride copolymers, ethylene-vinyl acetate copolymer, polyethylene terephthalate, nylon, polyethylene, polypropylene, polyvinylidine chloride (e.g., SARAN), paper, cloth and aluminum foil. The material used is preferably impermeable to the active agent. The material which forms this backing layer may be flexible or non-flexible. Preferably, a flexible backing layer is employed to conform to the shape of the body member to which the device is attached.

Preferably, the material which forms the backing layer, such as layer 16 of FIG. 1, is a film or a composite film. The composite can be a metallized (e.g., aluminized) film or a laminate of two or more films or a combination thereof. For example, a laminate of polyethylene terephthalate and polyethylene or a polyethylene/metallized polyethylene terephthalate/polyethylene laminate can be employed. The preferred polymers include polyethylene, polypropylene, polyvinyl chloride, polyesters such as polyethylene terephthalate (MYLAR) and polyvinylidine chloride (SARAN). Most particularly, a highly preferred composition of the present invention employs highly occlusive layers of polyethylene terephthalate (MYLAR) or polyvinylidine chloride (SARAN) as a backing layer such as backing member 16 of FIG. 1 in conjunction with an open cell polyurethane foam layer such as foam layer 12 of FIG. 1. Thus, while the polyethylene terephthalate or SARAN component is highly occlusive with respect to the materials in question, it is also relatively stiff or hard, and the use of a very soft and flexible open cell polyurethane foam layer such as foam layer 12 of FIG. 1, provides an excellent combination from the point of view of comfort and application to the user.

As noted above, the foam layer may be affixed to the backing layer by formation of the foam layer on the backing layer. For example, with respect to FIG. 1a, occlusive backing layer 16 is affixed to surface 17 of foam layer 12 by formation of foam layer 12 on the inner surface 9 of occlusive backing layer 16. Similar embodiments are depicted in FIGS. 2b, 2c, 5a and 6a. In such embodiments, the inner surface of the backing layer cannot be a low surface free energy polymer that does not adhere to urethanes, such as polyethylene, polypropylene, silicone and fluorocarbon-based films. The preferred polymers include polyurethanes, polyester elastomers such as HYTREL, polyether block amides such as PEBAX, polyacrylates, ethylene vinyl acetates, ethylene acrylate copolymers, ionomer resins such as SURLYN, polyvinyl chloride, polyvinylidene chloride (SARAN) and polyesters such as polyethylene terephthalate (MYLAR).

When the inner surface of the backing layer possesses a suitable surface energy relative to the polymerizing foam layer, the layer of polymer molecules at the surface of the foam layer is incorporated into the layer of molecules at the inner surface of the backing layer as the foam layer polymerizes. This eliminates the need for an adhesive to laminate the foam layer to the inner surface of the backing layer, but requires that the backing layer be occlusive.

As also noted above, the foam layer may be affixed to the backing layer by flame-bonding the foam layer to the backing layer. In such embodiments, the inner surface of the backing layer must again be one of the above-listed polymers possessing the surface energy needed for adhesion to urethane foams. In flame-bonding, the heat depolymerizes the foam which then repolymerizes so that the layer of polymer molecules at the surface of the foam layer is incorporated into the layer of molecules at the inner surface of the backing layer. Again, the need for an adhesive to laminate the foam layer to the inner surface of the backing layer is eliminated, but an occlusive backing layer is required.

As is described above, the backing layer may also be affixed to the foam layer by an adhesive layer. For example, with respect to FIG. 1, backing layer 16 is affixed to surface 17 of foam layer 12 by adhesive layer 18. In both embodiments, as discussed above, the adhesive layer may be active agent impermeable to prevent seepage of the active agent from the carrier layer to the backing layer, and should be active agent impermeable when the backing layer is not. The adhesive layer 18 and the backing layer 16 extend peripherally beyond the foam layer 12 about the entire periphery thereof so as to create an extended peripheral area of the backing layer 16 with the adhesive layer 18 peripherally extending beyond the foam layer 12 coextensively with the extended peripheral area of the backing layer 16. Therefore, another purpose of the adhesive layer 18 is to secure the device to the skin or mucosa.

As is also described above, the backing layer may optionally be affixed to the foam layer using an adhesive layer by first flame-bonding the foam layer to a film layer, which is then laminated to the backing layer by the adhesive layer. The flame bonding to the membrane is performed as described above. Suitable polymers for the film layer not only must possess the surface energy needed for adhesion to urethane foams, but also must resist migration of liquids in the foam layer to the adhesive layer. Polymers suitable for use as such film layers can be readily identified by those of ordinary skill in the art.

Thus, any adhesive capable of providing adhesion of the backing layer to the film layer or foam layer that is also capable of providing adhesion to the skin or mucosa will be suitable for use with the embodiment of FIG. 1 of the present invention. The degree of impermeability of the adhesive layer to the active agent would depend upon the active agent contained in the foam layer. Preferably, the adhesive layer is a pressure-sensitive adhesive suitable for contact with the skin or mucosa, e.g., dermatologically acceptable.

Active agent impermeable adhesives are typically coated onto the foam or backing layer in liquid form. The liquid form of the adhesives are obtained either by dissolution or suspension of the adhesive components in a liquid vehicle or emulsion or by heating a thermoplastic adhesive above its melt temperature. The adhesive layer is then either dried by evaporation of a liquid vehicle or emulsion or hardened by cooling thermoplastic material below its melt temperature. Active agent impermeable adhesives are thus defined as being impermeable to the active agent when the adhesive layer is substantially dry or hardened.

Examples of suitable pressure-sensitives for use in the present invention as the active agent impermeable adhesive layer includes some natural rubber and synthetic rubber adhesives, acrylic adhesives, and cross-linkable laminating adhesives. Examples of suitable natural rubber adhesives include R-1072 from B. F. Goodrich Co., No. 735 from C. L. Hathaway, and No. 5702 from Evans St. Clair. Examples of synthetic rubber adhesives include Jowatherm 270-00 and Jowatherm S-3202 from Jowath Cor. and 70-9416 from National Starch. Other suitable laminating adhesives include the Dow Corning laminating silicone adhesives and the Lord Corporation Tycel 7900 Series laminating adhesives. The adhesives most impermeable to most active agents are cross-linkable laminating adhesives, which are well-known to those of ordinary skill in the art.

When utilizing pressure-sensitive adhesives, as the thickness of the adhesive layer affixing the backing layer to the foam layer increases, the impermeability of the adhesive layer to the active agent also increases. To provide active agent impermeability to the adhesive layer, the thickness of the active agent impermeable adhesive layer 18 of FIG. 1 is that thickness that provides sufficient impermeability to the active agent (and if necessary, to the other components of the device with which the impermeable adhesive layer is in contact) so that the active agent does not seep out of the device as explained above. Typically, to obtain active agent impermeability, the impermeable adhesive layer joining the backing layer to the carrier layer will have a thickness between about two and about five mils, and preferably will have a thickness of about two mils.

Cross-linkable pressure-sensitive adhesives provide even greater impermeability of the adhesive layer to active agents and enhancers. By increasing the cross-linked density of the adhesive layer, an even greater barrier to active agent diffusion is provided.

Returning to the structure of the device shown in FIG. 1, the width of the adhesive layer 18 extending peripherally beyond the foam layer 12 about the entire periphery thereof coextensively with the backing layer 16 is that width which provides at least sufficient adhesion of the device to the skin or the mucosa of the host in combination with the active agent permeable adhesive layer 14. Impermeability to the active agent (and, if necessary, to the other components of the device with which the adhesive layer is in contact) so that the active agent does not seep out of the device, increases as the width of the layer increases.

Suitable widths will vary depending upon the active agent and the degree of impermeably decrease, and range from 1/16 to 2 inches, and preferably 1/8 to 1 inch. In most instances, the width will be from 1/4 to 1/2 inch depending upon the specific use. The width need not be uniform and may vary around the perimeter of the device, e.g., to provide a specific geometric shape or to provide a tab for removal of a protective liner.

The devices of the present invention may also include an active agent permeable adhesive layer between the foam layer and the skin or mucosa of the host, joining the device thereto. The active agent permeable adhesive layer is represented by layer 14 in FIG. 1. Certain embodiments utilize a second active agent permeable adhesive layer. For example, as shown in FIG. 2, active agent permeable adhesive layer 24 affixes rate-controlling polymer layer 22 to surface 15 of foam layer 12. The device is then affixed to the skin or mucosa of the host by active agent permeable adhesive layer 14, which is applied to the surface of the rate-controlling polymer layer 22 opposite to foam layer 12.

The active agent permeable adhesive layer that affixes the device to the skin or mucosa of the host is preferably dermatologically acceptable. Each active agent permeable adhesive layer is also preferably a pressure-sensitive adhesive. Any of the well-known, dermatologically acceptable, pressure-sensitive adhesives which permit drug migration therethrough can be used in the present invention.

Such suitable permeable adhesives include acrylic or methacrylic resins such as polymers of alcohol esters of acrylic or methacrylic acids and alcohols such as n-butanol, isopentanol, 2-methylbutanol, 1-methylbutanol, 1-methylpentanol, 2-methylpentanol, 3-methylpentanol, 2-ethylbutanol, isooctanol, n-decanol or n-dodecanol, alone or copolymerized with ethylenically unsaturated monomers such as acrylic acid, methacrylic acid, acrylamide, methacrylamides, N-alkoxymethyl acrylamides, N-alkoxymethyl methacrylamides, N-t-butylacrylamide, itaconic acid, vinyl acetate, N-branched alkyl maleamic acids wherein the alkyl group has 10–24 carbon atoms, glycol diacrylates, or mixtures of these monomers; polyurethane elastomers; vinyl polymers such as polyvinyl alcohol, polyvinyl ethers, polyvinyl pyrrolidone and polyvinyl acetates; urea formaldehyde resins; phenol formaldehyde resins, resorcinol formaldehyde resins; cellulose derivatives such as ethylcellulose, methylcellulose, nitrocellulose, cellulose acetate butyrate and carboxymethylcellulose; and natural gums such as guar, acacia, pectina, starch, destria, gelatin, casein, etc. Other suitable pressure-sensitive adhesives include polyisobutylene pressure-sensitive adhesives, rubber pressure-sensitive adhesives and silicone pressure-sensitive adhesives. The adhesives may also be compounded with tackifiers and stabilizers as is well-known in the art.

Adhesives that are preferred for their active agent permeability include acrylic copolymer adhesives such as Avery Chemical Company's AS-351 HSX, preferably at a coating weight of between 25 and 35 g/m$^2$. This pressure-sensitive adhesive is a cross-linkable polymer which provides a permanently tacky film having a total solids content of about 52%, Brookfield viscosity (LVT/Spindle No. 4/12 RPM at @ 25° C.) from about 15,000 to 25,000 cps. at a weight per gallon of about 7.4 lbs. It can also be diluted with hexane or toluene to a desired solids and/or viscosity range, particularly for use in conventional coating equipment.

Other such adhesives that can also be used for these purposes include an acrylic pressure-sensitive adhesive sold by National Adhesives under the designation DUROTAK 80-1054. This adhesive has a solids contents of 47.5%, a viscosity of 3,000 cps., and a plasticity (Williams) of 2.9 mm. It is generally used with a solvent system including ethyl acetate, heptane, isopropyl alcohol and toluene. Another such adhesive is sold by Monsanto under the designation GELVA Multipolymer Emulsion 2484, and comprises a stable aqueous acrylic emulsion pressure-sensitive adhesive having a solids content of 59% and a viscosity of 1,500 to about 2,300 cps. Examples of other acrylic adhesives include GELVA 788 and 733 from Monsanto, PS-41 from C. L. Hathaway, Vr-0833 from H. B. Fuller, ADCOT 73A207A from Morton Chemical, Nos. 80-2404, 80-1054, 72-9056 and 72-9399 from National Starch, Nos. E-2015, E-2067 and E-1960 from Rohm & Haas, M-6112 from Uniroyal, Inc. and Daratak 74 L from W. R. Grace. Suitable rubber adhesives include DUROTAK 36-6172 from National Starch and Morstik 118 from Morton Chemical. An example of a suitable silicone adhesive is X7-4502 from Dow Corning.

The active agent permeable adhesive layers preferably contain some of the active agent when the device is placed on the skin. This provides an initial active agent presence at the skin or mucosa and eliminates delay in absorption of the active agent if that is desired. Thus, the active agent is immediately available to the host. The initial active agent presence may be due to the migration through the adhesive layer or layers and, if present, rate-controlling layer, or to an amount of the active agent mixed in with the active agent permeable adhesive layer or layers or rate-controlling layer during manufacture. Thus, while either or both the active agent or active agent flux enhancer may be present in several of the laminate layers utilized, this may be the result of incorporation of the ingredients in only one of the layers, followed by migration of the ingredients to other layers.

The amount of the active agent or active agent enhancer present in the permeable adhesive layer or layers depends upon the initial drug presence desired, e.g., for a pulse dosage. For example, U.S. Pat. No. 4,031,894 discloses that 10–200 micrograms scopolamine base per cm$^2$ effective surface area is a suitable initial amount of active agent in the permeable adhesive layer.

The width (i.e., surface area) and thickness of the permeable adhesive layer for contact with the skin or mucosa is that width and thickness which provides sufficient permeability to the active agent or active agent enhancer and a suitable surface area to allow the dosage rate desired to the skin or mucosa. These widths and thicknesses are conventional in the art and therefore need not be discussed in detail here.

FIG. 1 depicts a peripheral adhesive layer in direct contact and/or adjacent to the permeable adhesive layer. However, this is not necessary and there may be a gap between the peripheral adhesive layer and the permeable adhesive layer, if desired.

The thickness and shapes of the peripheral and permeable adhesive layers in the embodiment depicted in FIG. 1 of the present invention need not be the same or correspond. This is a particular advantage to these embodiments of the invention in that the devices can be made to adhere to specific portions of the skin or mucosa by a primary means of the peripheral adhesive layers while not affecting the surface area of the permeable adhesive layer through which the active ingredient passes (i.e., the shape of the device can be varied without varying the surface area of the permeable adhesive layer which determines the amount of active agent delivered to the skin or mucosa).

With respect to the foam layers, such as foam layer 12 of FIG. 1, these are layers in which the active agent is physically reservoired. Stated another way, the active agent is contained in the interstices of the foam.

The foam may be a physically-blown foam; however, internally-blown foams, also known as water-blown foams, are preferred. While the preferred foam for use with the present invention is an internally-blown polyester or polyether-type polyurethane foam, the foam layers are defined for purposes of the present invention as including polyolefinic fine cell foams and porous films such as TESLIN manufactured by PPG of Pittsburgh, Pa., and CELGARD manufactured by Hoechst-Celanese.

As is well understood by those of ordinary skill in the art, polyurethane foams are generally prepared by the reaction of a polyester or polyether polyol with an organic polyisocyanate in the presence of a blowing agent and optionally in the presence of additional polyol-containing components, chain-extending agents, catalysts, surface-active agents, stabilizers, dyes, fillers and pigments. Suitable processes for the preparation of cellular polyurethane foams are disclosed in U.S. Pat. No. Re. 24,514, together with suitable machinery to be used in conjunction therewith. When water is added as the blowing agent, corresponding quantities of excess isocyanate to react with the water and produce carbon dioxide may be used.

It is possible to proceed with the preparation of the polyurethane plastics by prepolymer technique wherein an excess of organic polyisocyanate is reacted in a first step with the polyol to prepare a prepolymer having free isocyanate groups which is then reacted in a second step with water and/or additional polyol to prepare a foam. Alternatively, the components have reacted in a single working step commonly known as a "one-shot" technique of preparing polyurethanes. Furthermore, instead of water, low-boiling hydrocarbons such as pentane, hexane, heptane, pentene and heptene; azo compounds such as azohexahydrobenzodinitrile; halogenated hydrocarbons such as dichlorodifluoromethane, trichlorofluoromethane, dichlorodifluoroethane, vinylidene chloride and methylene chloride may be used as blowing agents.

Any suitable hydroxy-terminated polyester may be used such as are prepared, for example, from polycarboxylic acids and polyhydric alcohols. Any suitable polycarboxylic acid may be used such as oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, alpha-hydromuconic acid, beta-hydromuconic acid, alpha-butyl-alpha-ethyl glutaric acid, alpha,beta-diethylsuccinic acid, isophthalic acid, terephthalic acid, hemimellitic acid, and 1,4-cyclohexanedicarboxylic acid. Any suitable polyhydric alcohol, including both aliphatic and aromatic, may be used such as ethylene glycol, propylene glycol, trimethylene glycol, 1,2-butanediol, 1,3-butanediol, 1,4-butanediol, 1,2-pentanediol, 1,4-pentanediol, 1,5-pentanediol, 1,6-hexanediol, 1,7-heptanediol, glycerol, 1,1,1-trimethylolpropane, 1,1,1-trimethylolethane, 1,2,6-hexanetriol, alpha-methyl glucoside, pentaerythritol and sorbitol. Also included within the term "polyhydric alcohol" are compounds derived from phenols such as Bisphenol A. Adipic acid-based polyester polyols are preferred.

The hydroxyl-containing polyester may also be a polyester amide such as is obtained by including some amine or amino alcohol in the reactants for the preparation of the polyesters. Thus, polyester amides may be obtained by condensing an amino alcohol such as ethanolamine with the polycarboxylic acids set forth above or they may be made using the same components that make up the hydroxyl-containing polyester with only a portion of the components being a diamine such as ethylenediamine.

Any suitable polyether polyol may be used such as the polymerization product of an alkylene oxide or a mixture of alkylene oxides with a polyhydric compound. The preferred alkylene oxides include ethylene oxide, propylene oxide, butylene oxide, amylene oxide, and mixtures of these oxides. The polyether polyols are also preferably prepared from other starting materials such as tetrahydrofuran and alkylene oxide-tetrahydrofuran mixtures; epihalohydrins such as epichlorohydrin; as well as aralkylene oxides such as styrene oxide. The polyether polyols may have either primary or secondary hydroxyl groups. Included among the more preferred polyether polyols are polyoxyethylene glycol, polyoxypropylene glycol, polyoxybutylene glycol, and polytetramethylene glycol; block copolymers, for example, combination of polyoxypropylene and polyoxyethylene glycols, poly(1,2-oxybutylene) and polyoxyethylene glycols, poly(1,4-oxybutylene) and polyoxyethylene glycols, and random copolymer glycols prepared from blends of two or more alkylene oxides or from the sequential addition of two or more alkylene oxides.

The polyether polyols may be prepared by any known process such as, for example, the process disclosed by Encyclopedia of Chemical Technology, Vol. 7, pp. 257–62, published by Interscience Publishers, Inc. (1951) or in U.S. Pat. No. 1,922,459. Polyethers which are preferred include the alkylene oxide addition products of trimethylol propane, glycerine, pentaerythritol, sucrose, sorbitol, propylene glycol and 2,2'-(4,4'-hydroxyphenyl)propane and blends thereof having equivalent weights of from 100 to 10,000.

Organic polyisocyanates which may be employed include aromatic, aliphatic and cycloaliphatic polyisocyanates and combinations thereof. Representative of preferred types of these diisocyanates are m-phenylene diisocyanate, 2,4-toluene diisocyanate, 2,6-toluene diisocyanate, mixtures of 2,4- and 2,6-toluene diisocyanate, hexamethylene diisocyanate, tetramethylene diisocyanate, cyclohexane-1,4-diisocyanate, hexahydrotoluene diisocyanate (and isomers), naphthalene-1,5-diisocyanate, 1-methoxyphenyl-2,4-diisocyanate, 4,4'-diphenylmethane diisocyanate, 4,4'-bi-phenylene diisocyanate, 3,3'-dimethoxy-4,4'-bi-phenyl diisocyanate, 3,3'-dimethyl-4,4'-biphenyl diisocyanate and 3,3'-dimethyldiphenylmethane-4,4'-diisocyanate; triisocyanates such as 4,4',4"-triphenylmethane triisocyanate and toluene 2,4,6-triisocyanate; and tetraisocyanates such as 4,4'-dimethyldiphenylmethane- 2,2'-5,5'-tetraisocyanate and polymeric polyisocyanates such as polymethylene polyphenylene polyisocyante. Especially preferred because of their availability and properties are toluene diisocyanate, 4,4'-diphenylmethane diisocyanate and polymethylene polyphenylene polyisocyanate.

Crude polyisocyanates may also be used, such as crude toluene diisocyanate obtained by the phosgenation of a mixture of toluene diamines or crude diphenylmethane isocyanate obtained by the phosgenation of crude diphenylmethane diamine. The preferred crude isocyanates are disclosed in U.S. Pat. No. 3,215,652.

Chain-extending agents which may be employed in the preparation of polyurethane foams include those compounds having at least two functional groups bearing active hydrogen atoms such as water, hydrazine, primary and secondary diamines, amino alcohols, amino acids, hydroxy acids, glycols or mixtures thereof. A preferred group of chain-extending agents includes water, ethylene glycol, 1,4-butanediol and primary and secondary diamines which react more readily with the polymerizing polyurethane than does water, such as phenylenediamine, 1,4-cyclohexane-bis-(methylamine), ethylenediamine, diethylenetriamine, N-(2-hydroxypropyl)ethylenediamine, N,N'-di(2-hydroxypropyl)ethylenediamine, piperazine and 2-methylpiperazine.

Any suitable catalyst may be used including tertiary amines such as, for example, triethylenediamine, N-methylmorpholine, N-ethylmorpholine, diethylethanonamine, N-cocomorpholine, 1-methyl-4-dimethylaminoethylpiperazine, 3-methoxypropyldimethylamine, N,N,N'-trimethylisopropyl propylenediamine, 3-diethylaminopropyldiethylamine, dimethylbenzylamine, and the like. Other suitable catalysts are, for example, stannous chloride, dibutyltin di-2-ethyl hexanoate, stannous oxide, as well as other organometallic compounds such as are disclosed in U.S. Pat. No. 2,846,408.

A surface-active agent is generally necessary for production of high grade polyurethane foam according to the present invention, to prevent foam collapse or the formation of very large uneven cells. Numerous surface-active agents have been found satisfactory. Nonionic surface-active agents are preferred. Of these, the nonionic surface-active agents such as the well-known silicones have been found particularly desirable. Other surface-active agents which are operative, although not preferred, include polyethylene glycol ethers of long-chain alcohols, tertiary amine or alkanolamine salts of long-chain alkyl acid sulfate esters, alkyl sulfonic esters and alkyl arylsulfonic acids.

The foam layer of the present invention is preferably a high void volume open celled microcellular urethane foam. The void volume should be greater than 75%, preferably greater than 90%, more preferably greater than 95%, and most preferably greater than 97%. The foam layer should have a pore size of about 50 to about 100 pores per linear inch. Pore sizes between about 60 and about 90 pores per linear inch are preferred.

The foam layer should have a density of between about 1.5 and about 6.0 lbs./ft$^3$ with a density between about 1.5 and about 2.5 lbs./ft$^3$ being preferred. The thickness of the foam layer should be between about 90 and about 250 mils, with a thickness between about 125 and about 200 mils preferred.

As indicated above, urethane foam layers can be formed by sheet casting onto the occlusive liner backing layer against a restraining upper layer to produce a foam of a consistent thickness. The urethane foam can also be made into bun stock and peeled by conventional methods well-known to those of ordinary skill in the art. Pre-peeled roll stock is also commercially available. Regardless of how the foam layer is prepared, the foam should be hydrophilic to obtain uniform absorbtion of the active agent. Foams that are either inherently hydrophilic or treated to be hydrophilic are both suitable for use with the present invention.

In accordance with one embodiment of the present invention, the active agent may be pre-blended with the foam reactants before the foam is blown to obtain a uniform dispersion of the active agent throughout the foam layer. Such a reaction can be performed with any active agent that is not reactive with either the polyisocyanate, polyol or water foam reactants. The level of active agent in the foam layer is not contemplated to be so great as to dilute the reaction mixture of foam reactants to a degree that would interfere with the reaction.

The devices of the present invention optionally include a rate-controlling polymer layer depicted as layer 22 in FIG. 2. The polymers suitable for use as the rate-controlling polymer layer are conventional in the art and need not be discussed in detail here. Some preferred materials include, for example, polyethylene, polypropylene, ethylene vinyl acetate copolymer (EVA), polyester elastomers (e.g., HYTREL) and polyurethanes. Preferred rate-controlling polymer layer polymers are those which can be flame-bonded to or formed by sheet casting onto polyurethane foam so that the active agent permeable adhesive layer affixing the rate-controlling polymer layer to the foam layer can be omitted.

The rate of permeation of the active agent through the rate-controlling polymer layer depends upon factors such as the affinity of the active agent for the polymer layer, molecular size of the active agent, polymeric structure of the foam layer and the thickness of the layer. Therefore, the appropriate rate-controlling polymeric material and its thickness depend on the active agent used and the desired rate of permeation. The selection of a polymer layer and its thickness provides a means, if desired, for controlling the dosage rate to the skin or mucosa, and is essentially conventional to those of ordinary skill in the art.

The active agents of the present invention are defined as any liquid agents delivered topically to or through the skin. For purposes of the present invention, "liquid" active agents are defined as compounds or compositions that are liquid in their pure form at skin temperature (32° C.). Liquid active agents also include compounds and compositions that are solid in their pure form at skin temperature and dissolved or suspended in a carrier or binder that is liquid at skin temperature. Active agents that are liquid at skin temperature may also be combined with a binder to increase the viscosity of the active agent to ensure that the active agent is retained by the foam and gradually released. For purposes of the present invention, "liquid" active agents, carriers and binders are defined as including gels, colloids, dispersions, emulsions, solutions, and the like.

In a preferred embodiment of the present invention, the liquid active agent is liquid at skin temperature but solid at room temperature so that the active agent is in solid form in the foam layer until the laminate is attached to the skin or mucosa of the host. If necessary, carriers and binders are selected to provide an active agent that liquifies within this temperature range.

The active agents may be, for example, systemic or topical drugs. Individual active agents or mixtures thereof, if desired, can be employed. Any drug which passes through the skin or mucosa can be employed for internal or topical administration in the device of the invention, so long as the drug, alone, or in combination with a carrier or binder, is liquid at skin temperature and will pass through the permeable adhesive layer or layers present.

Suitable systemic drugs for administration by the devices of the present invention include psychoactive agents such as nicotine, pharmaceutically active compounds such as buprenorphine, ketovolac, selegiline, sertralin, lovastatin, sumatryptin, lorazepam, alprazolam, morphine and analogues thereof, benzodiazepines and tricyclic antidepressants, hormones such as estradiol and progesterone, and the like.

The quantity of active agent present in the foam layer is that quantity sufficient to provide a pharmaceutically or physiologically effective dosage rate of the active agent to a host in need thereof. This quantity can be readily determined by those of ordinary skill in the art without undue experimentation as shown in the examples set forth below. In general, the active agent is a pharmaceutically active compound present in the foam layer at levels between about 5 and about 75 percent by weight. This does not include levels of active agent enhancer, carrier or binder. When the active agent is nicotine, a nicotine concentration in the foam layer between about 0.5 and about 50 percent by weight is suitable, and a concentration between about 2 and about 30 percent by weight is preferred. A nicotine concentration of about 5 to 20 percent by weight is most preferred.

As noted above, a flux enhancer to promote the penetration of the active agent through the skin may be included in either the foam layer, rate-controlling polymer layer or the active agent permeable adhesive layers. Suitable enhancers include those described in U.S. Pat. No. 4,573,966, including, monovalent, saturated and unsaturated aliphatic and cycloaliphatic alcohols having 6 to 12 carbon atoms such as cyclohexanol, lauryl alcohol and the like; aliphatic and cycloaliphatic hydrocarbons such as mineral oil; cycloaliphatic and aromatic aldehydes and ketones such as cyclohexanone; N,N-di(lower alkyl) acetamides such as N,N-diethyl acetamide, N,N-dimethyl acetamide, N-(2-hydroxyethyl) acetamide, and the like; aliphatic and cycloaliphatic esters such as isopropyl myristate and lauricidin; N,N-di(lower alkyl) sulfoxides such as decylmethyl sulfoxide; essential oils, nitrated aliphatic and cycloaliphatic hydrocarbons such as N-methyl-2-pyrrolidone and azone; salicylates, polyalkylene glycol silicates; aliphatic acids such as oleic acid and lauric acid, terpenes such as cineole, surfactants such as sodium lauryl sulfate, siloxanes such as hexamethyl siloxane; mixtures of the above materials; and the like.

Examples of liquid carriers that may be combined with the active agent in the foam layer include polyethylene glycols, polypropylene glycols, polyester and polyether polyols, epoxidized linseed oils and simple liquid esters such as triethyl citrate, dicyclohexyl phthalate, diisodecyl adipate, fatty acids (oleic, lauric and the like), salts of fatty acids, fatty alcohols, fatty esters (CERAPHYLS and the like), terpenes and the like. The preferred liquid carriers include fatty acids, fatty esters, fatty alcohols, polyethylene glycols and polypropylene glycols.

Examples of binders that may be combined with the active agent in the foam layer include conventional hydrogels formed using water-soluble or water-insoluble gums or resins, with or without known cross-linking agents. The gums or resins include agarose, alginates, alkyl and hydroxyalkyl celluloses, such as hydroxyethyl cellulose and hydroxypropyl cellulose, amylopectin, arabinogalactin, carboxymethyl cellulose, carrageenan, eucheuma, fucoidan, furcellaran, gelatin, guar gum, gum agar, gum arabic, gum ghatti, gum karaya, gum tragacanth, hypenia, keratin laminaran, locust bean gum, pectin, polyacrylamide, poly(acrylic)acid and homologs, polyethylene glycol, poly(ethylene oxide), poly(hydroxyalkyl) methacrylate, polyvinyl alcohol, polyvinylpyrrolidone, propylene glycol alginate, starch and modified analogs, tamarind gum, N-vinyl lactam polysaccharides and xanthan gum. In addition, such hydrogels can be formed by the copolymerization and cross-linking of both hydrophilic and hydrophobic monomers, such as hydroxyalkyl esters of acrylic acid and methacrylamide, n-vinyl-2-pyrrolidone, alkyl acrylates and methacrylates, vinyl acetate, acrylonitrile and styrene. Other binders suitable for use with the present invention include veegum, higher molecular weight polyglycols, and the like.

The binders that are preferred for use with the present invention include cellulose esters, polyvinyl pyrrolidones and polyacrylates. Binders in accordance with the present invention can be prepared as a liquid, paste, semi-solid or solid that is combined with the active agent and incorporated into the foam layer.

In a preferred embodiment, the device contains a protective liner attached to the device at the surfaces to be adhered to the skin or mucosa, namely the active agent permeable adhesive layer and, if present, the peripheral adhesive layer. The protective liner may be made of the same material suitable for use in the backing layer as discussed above. Such material is preferably made removable or releasable from the adhesive layers by, for example, conventional treatment with silicon, Teflon or other suitable coating on the surface thereof. The removal of the device from the protective liner may also be provided by mechanical treatment of the protective liner, e.g., by embossing the protective liner.

The protective liner, however, can comprise various layers, including paper or paper-containing layers or laminates; various thermoplastics, such as extruded polyolefins, such as polyethylene; various polyester films; foil liners; other such layers, including fabric layers, coated or laminated to various polymers, as well as extruded polyethylene, polyethylene terephthalate, various polyamides, and the like. The protective liner can also comprise vacuum metallized films such as metallized polyester or polypropylene formed by vapor deposition of aluminum for UV and oxygen resistance.

A particularly preferred embodiment of the protective liner of the present invention includes a laminate of an outer foil layer and an inner layer of plastic, such as polyethylene or the like, which is rendered releasable not only by means of a siliconized coating, but which also includes an embossed or roughened surface. Embossment of the surface can be accomplished by a number of conventional methods. In general, preparation of embossed surfacing can be accomplished by the use of male-female tooling, preferably enhanced by the application of heat. The principal intention of this embossment process is to roughen the surface or render it uneven so that less than the entire surface will be in physical contact with the corresponding adhesive layer.

The actual pattern of embossment carried out can vary, and in some instances may involve embossment of large contiguous areas of the protective liner. Preferably, approximately 30% of the surface of the protective liner will thus be embossed. The particular design of the embossment, such as the production of a grainy texture or the like, is a matter of choice within the parameters discussed above. The presence of the embossed surface on the inner surface of the protective liner is thus extremely significant in preventing the protective liner from sticking or adhering to the adhesive layer or layers, which would cause the liner to fail to properly separate from the adhesive layer or layers when it is desired to use the device of the present invention. This ease of operation is an important element in commercialization of these devices. The selection of a particular protective liner will also depend upon other ultimate requirements of the particular device in question, including whether there is a desire for a transparent or opaque liner, etc.

It can thus be seen that although substantially the entire surface of the protective liner is in contact with the adhesive layer or layers, the seal provided to the adhesive layer or layers by the protective liner is "peelable" or releasable, by merely pulling apart the edge of the protective liner. At the same time, when this is done, the adhesive layer or layers for contact with the skin or mucosa remain in contact with the surface of the carrier layer and a peripherally extended backing area, if present, because of the coefficient of adhesion between the adhesives and these layers vis-a-vis the coefficient of adhesion between these adhesive layers and the coated release surface of the protective liner.

The host to which an active agent is administered by means of the inventive device may be any host on which a drug or other active agent has the desired effect. The host may be, for example, a mammal such as a human being, or, for that matter, any warm-blooded or cold-blooded animal. The advantage of administering the active agent may be therapeutic or experimental. The device of this invention may also be used for any other advantageous purpose.

The various layers of the device of the present invention may be combined to form a laminate by methods conventional in the art. However, the present invention includes an inventive process for attaching the foam layer to the backing layer without an adhesive by forming the foam layer on the backing layer, an inventive process for incorporating the active agent into the foam layer by adding the active agent to a prepolymer solution before polymerizing it to form the foam layer, as well as an inventive process for flame-bonding the foam layer to the rate-controlling polymer layer on the backing layer.

As described above, when the foam layer is urethane foam, the foam layer can be provided by pre-peeled roll stock, or it can be peeled from bun stock prepared by methods conventional to those of ordinary skill in the art. The foam layer can also be made to gauge by sheet casting the foam onto a first layer against a restraining upper layer to produce a foam of a consistent thickness. Preferably, the first layer is the backing layer so that a laminate of the backing layer and foam layer is formed by the polymerization of the foam layer on the backing layer.

The foam layer is formed on the backing layer by metering together a first stream containing an isocyanate polymer or prepolymer and a second stream containing the catalyst, water, surfactant stabilizer, an optional polyester or polyether polyol, and the active drug substance, if any. The mixture is then dispensed across a moving web of backing layer material.

More particularly, the two streams are metered together in a mixing/dispensing unit that oscillates back and forth across the moving web, laying down a coating of the foam formula. The reaction is initiated as the streams are brought together in the mix head and consists of two balanced parts.

First there is polymerization followed by foaming. Carbon dioxide is liberated by a side reaction of the isocyanate and water. This gas reduces the density of the polymer and creates the foam matrix. As the foam rises and the polymer is still forming, the coated backing is run through a nip roll which restricts and controls the final thickness of the sheet cast laminate.

In one embodiment of the present invention, the backing layer has a sufficient surface area and is shaped so that when it is attached to the foam layer, it overlaps the foam layer completely so that it surrounds the perimeter of the foam layer. When the foam layer is attached to the backing layer by an adhesive layer, this can be accomplished either by first die-cutting the foam layer and combining the die-cut foam pieces with the backing layer. Alternatively, the backing and foam layers can be combined prior to die-cutting. Die-cutting, whenever mentioned herein, is carried out by processes well-known in the laminating art.

When the foam layer is formed on the backing layer, it is not practical to die-cut the foam layer. Instead, the prepolymer solution is applied in the pattern of the foam layer to the backing layer prior to foaming by conventional pattern coating or printing methods such as stenciling, silk screening, and the like.

The liquid active agent, together with any active agent enhancers, carriers or binders, can be incorporated into the foam layer by any one of several methods. When the foam layer is laminated to the backing layer using commercially available pre-peeled roll stock or roll stock peeled in-house from bun stock, the liquid active agent, and any other ingredients, can be incorporated into the foam layer by conventional coating techniques, so that the liquid active agent is absorbed into the foam layer. Generally, the foam layer is uniformly coated with the liquid active agent and other ingredients by coating techniques such as roll, gravure, nip, or transfer coating, and the like. Such a coating step can be performed in line with the laminating equipment combining the various backing, foam and adhesive layers.

As noted above, the present invention includes an alternative method by which the active agent is incorporated into the foam layer. In particular, the active agent can be added to the catalyst solution prior to foaming the foam layer. The active agent, including any active agent enhancers, binders or carriers, is added to a solution of the catalyst, surfactant stabilizer, an optional polyester or polyether polyol and water in quantities effective to form a cellular urethane foam. The solution is then brought into contact with a solution containing an effective quantity of an isocyanate polymer or prepolymer so that a cellular urethane foam is formed containing the active agent.

The foam is formed into foam layers following the procedures described above for foams not containing liquid active agents. In particular, the foam may be formed into bun stock and peeled to form active agent-containing foam layers by methods conventional in the art. Foam layers containing active agents may also be made to gauge by sheet casting between a first layer and a restraining roll or layer as described above.

The restraining layer is removed and the active agent-containing foam layer is then peeled from the first layer. The foam layer can then be laminated to the backing layer as described above, or backing layers may be selected so that the foam layer will adhere to as it is polymerizing, without the use of adhesive, and form on the backing layer, as described above. As noted above, a restraining roll or layer may be used to control the final thickness of the foam layer.

Regardless of how the foam layer is formed, or whether the liquid active agent is incorporated therein prior to formation, an adhesive layer is provided to the laminate for affixing the laminate to the skin or mucosa of the host. This adhesive layer is applied to the extended peripheral area of the backing layer, if present, and to the outermost layer of the laminate opposite the backing layer. This is the foam layer, when no rate-controlling polymer layer is present, and the rate-controlling polymer layer, when such a layer is present. When the foam layer is laminated with an adhesive to the backing layer, then the adhesive layer providing a means for affixing the device to the host can be applied either before or after the foam layer and backing layer are laminated together. When the foam layer is formed on the backing layer, then the adhesive layer providing a means for affixing the device to the host can only be applied after the foam layer and backing layer are formed together.

As noted above, certain embodiments include a rate-controlling polymer layer affixed to the foam layer on the surface to be applied to the skin or mucosa of the host. This polymer layer is either adhered to the foam layer by an active agent permeable adhesive layer, or, this layer can also be flame-bonded to the foam layer. The adhesive laminating techniques for combining the foam and rate-controlling polymer layers are essentially conventional. The foam layer can be bonded to essentially any film or non-woven layer by exposing the foam to a flame knife before the mating nip.

The use of flame knives to flame-bond foam layers to films and non-wovens is essentially conventional and well understood by those or ordinary skill in the art. The flame depolymerizes the foam which then repolymerizes so that the surface layer of foam polymer molecules is incorporated into the surface layer of molecules of the film, paper or non-woven substrate, thereby adhering to the substrate without the use of an adhesive. Thus, the foam layer can also be flame-bonded to the backing layer. Plastic films for the flame-bonding of foam layers should possess sufficient surface energy to adhere to urethanes. Suitable films are described above with respect to the backing layer. Films which are not suitable include the above-listed polyethylene, polypropylene, silicone and fluorocarbon based films. Thus, the foam layer, occlusive backing layer and rate-controlling polymer layer can be flame-bonded together. When all three layers are flame-bonded, the only adhesive layer required will adhere the rate-controlling polymer layer, or an extended periphery of the occlusive backing layer, if present, and thus the laminate, to the skin or mucosa of the host.

As will be readily understood, the foam layer can also be foamed between the occlusive backing layer and the rate-controlling polymer layer. Again, the only adhesive layer that will be required will adhere the laminate to the skin or mucosa of the host.

The device, once formed, may be kept sealed in an air-tight pouch prior to use. The device of the present invention is used in the same manner as those devices which are conventional in the prior art. In most instances, the releasable protective liner attached to the skin-side surface of the adhesive layer or layers of the device for contact with the skin or mucosa of the host is removed in such surface of the adhesive layer or layers as applied to the desired area of the skin or mucosa.

The following non-limiting examples set forth hereinbelow illustrate certain aspects of the invention, but are not meant in any way to restrict the effective scope of the invention. All parts and percentages are by weight unless otherwise noted, and all temperatures are in degrees Celsius.

EXAMPLE 1

A double disc transdermal patch was prepared using as the polyurethane foam layer a commercially available pre-peeled roll stock. A roll of SCOTT polyurethane foam having a density of about 1.6 lbs./ft$^3$, a pore size of about 60 pores per linear inch, and a thickness of about ⅛ inch was flame-bonded to a 1 mil thick film extruded from PC-38-200 polyurethane resin supplied by Morton International. The foam and membrane were flame-bonded by melting the foam surface with flame and mating it with the membrane with pressure The foam with the flame-bonded membrane was coated with a warm 4% agarose aqueous hydrogel solution containing 3% nicotine. The gel solidified in a few minutes and 10 cm$^2$ discs were die-cut having an average thickness of 5 mil and an average weight of 670 mg. The discs were placed on a release liner with the membrane side up. The membrane layers were laminated to 20 cm$^2$ discs of 1 mil thick MELINEX™ polyethylene terephthalate film from ICI, using a 2 mil thick layer of GELVA 737 (Monsanto) acrylic pressure-sensitive adhesive. The resulting laminate corresponded to the embodiment depicted in FIG. 11a.

The nicotine content of the patches was determined with High Performance Liquid Chromatography (HPLC) to obtain 24 mg of nicotine per 10 cm$^2$ of patch. The in-vitro nicotine release of the foam laminate through a skin substitute was measured using the Franz Diffusion Cell Method. In this method, an excised human or animal skin was overlayed with a transdermal patch in such a way that the adhesive side of the patch was in contact with the skin. This patch/skin lamination was then mounted onto a Franz Diffusion Cell on top of the lower, or receiving, chamber of the cell, which was filled with isotonic saline at pH 7.4. This saline solution contacts the skin at the top of the chamber. The temperature of the isotonic solution was maintained at 32° C. by thermostatically controlled water circulation through a jacket surrounding the receiving chamber. Homogeneous distribution of temperature was achieved by a small magnetic stirrer. Thus, the skin was held under conditions approximating the living state.

A 10 cm$^2$ HABITROL transdermal nicotine patch (Lot No. 1028200) having a nicotine content of 17.5 mg/10 cm$^2$ was used as a control. At 2 hours, 4 hours, 9.5 hours and 24 hours, 1–2 mL of the saline solution was withdrawn from the receiving chamber and analyzed by HPLC. The drug concentration in the saline solution sample was calculated using calibration standards and the drug permeation kinetic profile through the skin was thus obtained.

The skin utilized in this example was from a 61-year-old white female thigh obtained from Michigan Tissue Bank. The results are presented in the table below:

TABLE I

| | Nicotine In-Vitro Flux Through Skin (mg/10 cm$^2$) | | | |
|---|---|---|---|---|
| | 2 hr. | 4 hr. | 9.5 hr. | 24 hr. |
| Example | 1.09 ±0.1 | 2.61 ±0.35 | 5.54 ±0.99 | 8.75 ±1.71 |
| Control* | 1.63 ±0.14 | 2.84 ±0.24 | — | 9.63 ±0.93 |

*Habitrol Lot No. 1028200

EXAMPLE 2

A double disc transdermal patch was prepared by formation of the foam layer on the rate-controlling polymer layer from a urethane prepolymer having an aqueous nicotine solution dispersed therein. A 10% by weight aqueous nicotine solution was prepared by dissolving 10 g nicotine in 90 g water. 50 g of the nicotine solution was then mixed in a 1:1 weight ratio with a urethane prepolymer (HYPOL 2002, Hampshire Chemical Corp., Lexington, Mass.).

The water in the nicotine solution initiated the foaming reaction. The mixture was immediately poured onto a polyurethane film layer extruded from the Morton International PC-38-200 resin, having a thickness of 1.5 mil, which serves as a rate-controlling polymer film layer. The polyurethane film was supported by a stainless steel metal plate, which was aligned to within 10 mils of an equivalent metal plate bearing a release liner, so that a foam layer directly laminated to a single rate-controlling polyurethane film layer was produced. The predetermined displacement of the two metal plates confined the reacting foam mixture to control the thickness of the foam layer. Any excess foam spilled out the sides of the two metal plates and was trimmed.

The side of the polyurethane film opposite the foam layer was placed on a release liner coated with a 2 mil thick layer of GELVA 737 (Monsanto) acrylic pressure-sensitive adhesive. 1.2 cm$^2$ discs were die-cut and were then laminated to a MYLAR occlusive layer as in Example 1. The resulting laminate corresponded to the embodiment depicted in FIG. 3.

EXAMPLE 3

A double disc transdermal patch was prepared as in Example 2, substituting for the polyurethane film a 2.5 mil thick EVA film extruded from UE-635-000 EVA resin supplied by UsI-Quantum having a 9% vinyl acetate content.

EXAMPLE 4

A double disc transdermal patch was prepared as in Examples 2 and 3, initially substituting a second release liner for the polyurethane or EVA film when casting the foam, so that a foam layer is obtained without a rate-controlling polymer film layer laminated thereto.

The nicotine content of the patches and the in vitro nicotine release of the foam laminate through a skin substitute or measured as in Example 1. The skin used for the in vitro study was from the back of a 76-year-old white female obtained from Michigan Tissue Bank. The control was a coextruded monolithic nicotine patch prepared according to the procedure disclosed in Example 4 of copending and commonly owned U.S. patent application Ser. No. 861,534, filed Apr. 1, 1992, the disclosure of which is hereby incorporated herein by reference thereto. The monolithic patch tested equivalent in vitro to the commercially available HABITROL™ patch. The nicotine content measured for each patch is set forth below in Table II.

TABLE II

| Example | Nicotine Content | Foam Wt. | % Nicotine In Foam |
| --- | --- | --- | --- |
| 2 | 16.2 mg/10 cm$^2$ | 289.4 mg | 5.6 wt/% |
| 3 | 24.0 mg/10 cm$^2$ | 354.2 mg | 6.8 wt/% |
| 4 | 50.8 mg/10 cm$^2$ | 886.2 mg | 5.7 wt/% |

The control patch had a nicotine content of 16.7 mg/10 cm$^2$. The in vitro release rates are set forth below in Table III.

TABLE III

| | Nicotine in vitro Flux Through Skin [mg/10 cm$^2$] | | | |
| --- | --- | --- | --- | --- |
| Example | 2 hours | 4 hours | 8 hours | 24 hours |
| Control | 0.68 | 1.41 | 3.10 | 5.57 |
| 2 | 0.62 | 1.26 | 2.14 | 4.67 |
| 3 | 0.87 | 1.78 | 3.25 | 7.71 |
| 4 | 1.08 | 2.33 | 3.53 | 11.55 |

The test results demonstrate that the transdermal patches of the present invention deliver nicotine at rates equivalent to commercially available patches.

As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A process for assembling a device for the controlled release of an active agent to the skin or mucosa of a host, said process comprising the steps of:

(a) incorporating a liquid active agent into an internally blown fully reticulated microcellular polyester or polyether cellular urethane foam layer having a first surface and a second surface, and a void volume greater than about 75%;

(b) providing a backing layer having an inner surface and an outer surface and laminating the second surface of said foam layer to said inner surface of said backing layer so that a laminate of said foam layer and said backing layer is formed wherein said active agent cannot permeate from said second surface of said foam layer to said outer surface of said backing layer; and (c) providing said laminate with means for securing said laminate to said skin or mucosa of said host so that said active agent can be controllably released from said first surface of said foam layer thereto.

2. The process of claim 1, wherein said step of providing said laminate with means for securing said laminate to said skin or mucosa of said host comprises the step of applying to said laminate an active agent permeable adhesive layer adapted to adhere said first surface of said foam layer to said skin or mucosa of said host.

3. The process of claim 1, wherein said step of providing a backing layer comprises the steps of providing a backing layer having a greater surface area than said foam layer and laminating said second surface of said foam layer to said inner surface of said backing layer so that said greater surface area of said backing layer extends peripherally beyond said foam layer about the entire periphery thereof so as to create an extended peripheral area of said backing layer, and said step of providing said laminate with means for securing said first surface of said foam layer to said skin or mucosa of said host comprises the step of adapting said inner surface of said extended peripheral area of said backing layer to adhere to said skin or mucosa of said host so that said laminate firmly adheres thereto.

4. The process of claim 3, wherein said adapting step comprised coating said inner surface of said extended peripheral area of said backing layer with an adhesive layer adapted to adhere said backing layer to said skin or mucosa of said host.

5. The process of claim 4, wherein said step of providing said laminate with means for securing said laminate to said skin or mucosa of said host further comprises the step of coating said first surface of said foam layer with an active agent permeable adhesive layer.

6. The process of claim 1, further comprising the step of affixing to said first surface of said foam layer means for controlling the rate at which said active agent is released from said first surface of said foam layer to said skin or mucosa of said host.

7. The process of claim 6, wherein said affixing step comprises coating said first surface of said foam layer with an active agent permeable adhesive layer capable of controlling said rate at which said active agent is released from said first surface of said foam layer to said skin or mucosa of said host.

8. The process of claim 6, wherein said affixing step comprises laminating a rate-controlling polymer layer to said first surface of said foam layer.

9. The process of claim 8, wherein said laminating step comprises coating said first surface of said foam layer with an adhesive layer and affixing said rate-controlling polymer layer to said adhesive layer.

10. The process of claim 8, wherein said step of providing said laminate with means for securing said laminate to said skin or mucosa of said host comprises coating said rate-controlling polymer layer on the surface opposite said foam layer with an active agent permeable adhesive layer.

11. The process of claim 1, wherein said backing layer comprises an active agent impermeable material.

12. The process of claim 1, wherein said backing layer comprises one or more layers of an occlusive material, wherein each layer of material is independently selected from the group consisting of cellophane, cellulose acetate, ethyl cellulose, plasticized vinyl acetate-vinyl chloride copolymers, ethylene-vinyl acetate copolymers, polyurethanes, polyester elastomers, polyesters, polyether block amides, polyacrylates, ethylene acrylate copolymers, ionomer resins, nylon, polyethylene, polypropylene, polyvinylidene chloride, paper, cloth and aluminum foil.

13. The process of claim 12, wherein said inner surface of said backing layer comprises a layer of materials selected from the group consisting of polyurethanes, polyester elastomers, polyether block amides, polyacrylates, ethylene vinyl acetates, ethylene acrylate copolymers, ionomer resins, polyvinyl chloride, polyvinylidene chloride and polyesters.

14. The process of claim 1, wherein said adhesive layer adapted to adhere said laminate to said skin or mucosa of said host comprises a pressure-sensitive adhesive material selected from the group consisting of polyisobutylene adhesives, silicone adhesives, acrylic adhesives and synthetic rubber adhesives.

15. The process of claim 14, wherein said acrylic pressure-sensitive adhesive is an alcohol ester of polyacrylic or polymethacrylic acid.

16. The process of claim 15, wherein the alcohol of said alcohol ester of polyacrylic or polymethacrylic acid is selected from the group consisting of n-butanol, isopentanol, 2-methylbutanol, 1-methylbutanol, 1-methylpentanol, 2-methylpentanol, 3-methylpentanol, 2-ethylbutanol, isooctanol, n-decanol and n-dodecanol.

17. The process of claim 16, wherein said esters of polyacrylic acid and polymethacrylic acid are copolymerized with one or more ethylenically unsaturated monomers selected from the group consisting of acrylic acid, methacrylic acid, acrylamide, methacrylamide, N-alkoxymethyl acrylamide, N-alkoxymethyl methacrylamide, N-t-butylacrylamide, itaconic acid, vinyl acetate, N-branched alkyl malemic acid with alkyl groups containing from 10 to 24 carbon atoms and glycol diacrylates.

18. The process of claim 2, wherein said active agent permeable adhesive layer comprises a dermatologically acceptable pressure-sensitive adhesive selected from the group consisting of polyurethane elastomers, polyvinyl alcohol, polyvinyl ethers, polyvinyl pyrrolidone, polyvinyl acetate, urea formaldehyde resins, phenol formaldehyde resins, resorcinol formaldehyde resins, ethylcellulose, methylcellulose, nitrocellulose, cellulose acetate butyrate, carboxymethyl cellulose, guar gum, acacia gum, pectina gum, destria gum, gelatin and casein.

19. The process of claim 1, wherein said urethane foam has a void volume greater than about 95%.

20. The process of claim 1, wherein said foam layer has a pore size of about 50 to about 100 pores per linear inch.

21. The process of claim 1, wherein said urethane foam has a density of between about 1.5 and about 6.0 lbs./ft$^3$.

22. The process of claim 1, wherein said foam layer has a thickness of between about 90 and about 250 mils.

23. The process of claim 1, wherein said urethane foam comprises a hydrophilic foam.

24. The process of claim 1, wherein said liquid active agent is selected from the group consisting of nicotine, buprenorphine, ketovolac, selegiline, setralin, lovastatin, sumatryptin, lorazepam, estradiol, progesterone, alprazolam, morphine, and benzodiazepines.

25. The process of claim 24, wherein said active agent is nicotine.

26. The process of claim 1, wherein said liquid active agent comprises one or more additives selected from the group consisting of active agent flux enhancers, active agent carriers and active agent binders.

27. The process of claim 26, wherein said active agent flux enhancer is selected from the group consisting of monovalent, saturated aliphatic alcohols having from 6 to 12 carbon atoms, monovalent, unsaturated aliphatic alcohols having from 6 to 12 carbon atoms, monovalent, saturated cycloaliphatic alcohols having from 6 to 12 carbon atoms, monovalent, unsaturated cycloaliphatic alcohols having from 6 to 12 carbon atoms, aliphatic hydrocarbons, cycloaliphatic hydrocarbons, cycloaliphatic aldehydes, aromatic aldehydes, cycloaliphatic ketones, N,N-di(lower alkyl)acetamides, aliphatic esters, cycloaliphatic esters, N,N-di(lower alkyl)sulfoxides, essential oils, nitrated aliphatic hydrocarbons, nitrated cycloaliphatic hydrocarbons, salicylates, polyalkylene glycol silicates, aliphatic acids, terpenes, surfactants and siloxanes.

28. The process of claim 26, wherein said active agent carrier is selected from the group consisting of polyethylene glycols, polypropylene glycols, polyester polyols, polyether polyols, epoxidized linseed oils, triethyl citrate, dicyclohexyl phthalate, diisodecyladipate, fatty acids, salts of fatty acids, fatty alcohols and terpenes.

29. The process of claim 26, wherein said active agent binder is selected from the group consisting of hydrogels formed using water-soluble and water-insoluble gums and resins.

30. The process of claim 26, wherein the combination of said liquid active agent with said one or more additives is solid at room temperature and liquid at skin temperature.

31. The process of claim 8, wherein said rate-controlling polymer layer comprises at least one ingredient selected from the group consisting of said active agent, liquid active agent flux enhancers, active agent carriers and active agent binders.

32. The process of claim 8, wherein said rate-controlling polymer layer comprises a material selected from the group consisting of polypropylene, polyethylene, ethylene vinyl acetate, polyether polyurethanes, polyether block amides, ethylene methacrylic acid copolymers, ethylene acrylic acid copolymers and copolymers of polyether prepolymers and polybutylene terephthalate and polyisobutylene terephthalate.

33. The process of claim 1, wherein said step of incorporating said liquid active agent into said foam layer comprises the step of coating said foam layer with a solution of said active agent so that said active agent is absorbed into said foam layer.

34. The process of claim 1, wherein said inner surface of said backing layer comprises a material capable of adhering to urethane foam formed thereon and said laminating step comprises the steps of:

providing a solution comprising a polyisocyanate;

contacting said polyisocyanate solution with an aqueous solution comprising a urethane catalyst, so that a prepolymer solution is formed; and coating said prepolymer solution between said inner surface of said backing layer and a retaining layer so that said prepolymer solution forms a microcellular urethane foam layer on said inner surface of said backing layer without an adhesive.

35. The process of claim 34, wherein said polyisocyanate is selected from the group consisting of toluene diisocyanate, 4,4'-diphenylmethane diisocyanate and polyphenylene polymethylene polyisocyanate.

36. The process of claim 34, wherein said polyisocyanate comprises a copolymer of a polyisocyanate with a polyester or polyether polyol.

37. The process of claim 36, wherein said polyol is an adipic acid based polyester polyol.

38. The process of claim 34, wherein said aqueous solution comprises a polyester or polyether polyol.

39. The process of claim 38, wherein said polyol is an adipic acid based polyester polyol.

40. The process of claim 34, wherein said aqueous solution further comprises said liquid active agent.

41. The process of claim 40, wherein said liquid active agent is nicotine.

42. The process of claim 36, wherein said polyol is an addition product of an alkylene oxide with a polyhydric compound selected from the group consisting of trimethylol propane, glycerine, pentaerythritol, sucrose, sorbitol, propylene glycol and 2,2'-(4,4'-hydroxyphenyl)propane.

43. The process of claim 38, wherein said polyol is an addition product of an alkylene oxide with a polyhydric compound selected from the group consisting of trimethylol propane, glycerine, pentaerythritol, sucrose, sorbitol, propylene glycol and 2,2'-(4,4'-hydroxyphenyl)propane.

* * * * *

UNITED STATES PATENT AND TRADEMARK OFFICE
CERTIFICATE OF CORRECTION

PATENT NO. : 5,503,844
DATED : April 2, 1996
INVENTOR(S) : Kwiatek et al.

It is certified that error appears in the above-identified patent and that said Letters Patent is hereby corrected as shown below:

Column 24, line 62, "comprised" should read --comprises--.

Signed and Sealed this

Thirteenth Day of August, 1996

*Attest:*

BRUCE LEHMAN

*Attesting Officer*　　　*Commissioner of Patents and Trademarks*